(12) United States Patent
Saraf

(10) Patent No.: US 7,846,714 B2
(45) Date of Patent: *Dec. 7, 2010

(54) SYNTHESIS OF CHEMICAL TAGS

(75) Inventor: Ravi F. Saraf, Briar Cliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/927,826

(22) Filed: Oct. 30, 2007

(65) Prior Publication Data

US 2008/0108516 A1    May 8, 2008

Related U.S. Application Data

(60) Division of application No. 10/608,094, filed on Jun. 30, 2003, now abandoned, which is a continuation of application No. 09/916,439, filed on Jul. 30, 2001, now Pat. No. 6,632,612, and a continuation of application No. 09/668,140, filed on Sep. 25, 2000, now abandoned, which is a continuation of application No. 09/154,584, filed on Sep. 17, 1998, now abandoned.

(51) Int. Cl.
- *C12M 1/00* (2006.01)
- *C12M 1/34* (2006.01)
- *C07H 21/02* (2006.01)
- *C07H 21/04* (2006.01)
- *C12Q 1/68* (2006.01)

(52) U.S. Cl. .............. 435/283.1; 435/287.1; 435/287.2; 536/23.1

(58) Field of Classification Search .................. None
See application file for complete search history.

(56) References Cited

U.S. PATENT DOCUMENTS

| | | |
|---|---|---|
| 5,449,603 A | 9/1995 | Nielson et al. |
| 5,605,662 A | 2/1997 | Heller et al. |
| 5,652,096 A | 7/1997 | Cimino |
| 6,017,696 A * | 1/2000 | Heller .......................... 435/6 |
| 6,274,373 B1 | 8/2001 | Virtanen |
| 6,312,901 B2 | 11/2001 | Virtanen |
| 6,331,275 B1 | 12/2001 | Virtanen |
| 6,342,349 B1 | 1/2002 | Virtanen |

FOREIGN PATENT DOCUMENTS

| | | |
|---|---|---|
| EP | 0 987 653 A1 | 3/2000 |
| EP | 99 30 6969 | 3/2000 |
| JP | 2000-101167 | 4/2000 |

OTHER PUBLICATIONS

Zhu, Z. et al., NUcl. acids res., vol. 22, pp. 3418-3422 (1994).*
M. Schena et al., "Parallel Human Genome Analysis: Microarray-Based Expression Monitoring of 1000 Genes" Proc. Natl. Acad. Sci., vol. 93, pp. 10614-10619, 1996.
M. Wold, "Repliction Protein A: A Heterotrimeric, Single-Stranded DNA-Binding Protein Required for Eukaryotic DNA Metabolism," Annu. Rev. Biochem., vol. 66, pp. 61-92, 1997.
M. Cox et al., "On the Role of Single-Stranded DNA Binding Protein in recA Protein-Promoted DNA Strand Exchange," The Journal of Biological Chemistry, vol. 258, No. 4, pp. 2577-2585, 1983.
J. Jiricny et al., "Mismatch-Containing Oligonucleotide Duplexes Bound by the *E. Coli* mutS-Encoded Protein," Nucleic acids research, vol. 16, No. 6, pp. 7843-7853, 1988.
A. Lishanski et al., "Mutation Detection by Mismatch Binding Protein, MutS, in Amplified DNA: Application to the Cystic Fibrosis Gene," Biochemistry, vol. 91, pp. 2674-2678, 1994.
E. Palecek, "Probing DNA Structure With Osmium Tetroxide Complexes In Vitro," Methods in Enzymology, vol. 212, pp. 139-155, 1992.
R. Turton, "The Quantum Dot", A Journey Into the Future of Microelectronics, (Oxford Press, 1995), Title pp. i-x and pp. 1-212.

* cited by examiner

*Primary Examiner*—Teresa E Strzelecka
(74) *Attorney, Agent, or Firm*—Connolly Bove Lodge & Hutz LLP; Louis J. Percello

(57) ABSTRACT

A method for forming a biological chemical tag. At least one double stranded DNA molecule is provided. At least a portion of the at least one double stranded DNA molecule is denatured. At least one chemical moiety that prohibits recrystallization of the at least one denatured portion to which the at least one chemical moiety is attached is attached to at least one nucleotide in the at least one denatured portion of the at least one double stranded DNA molecule.

20 Claims, 6 Drawing Sheets

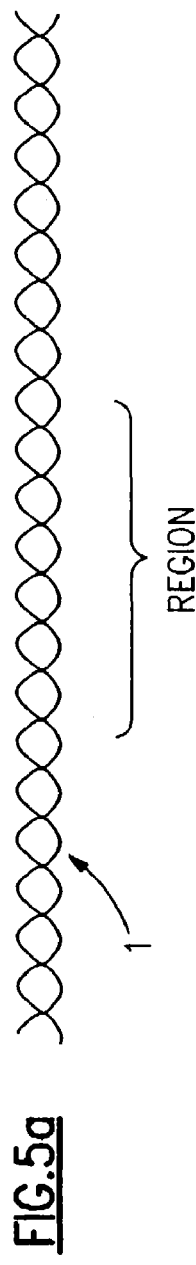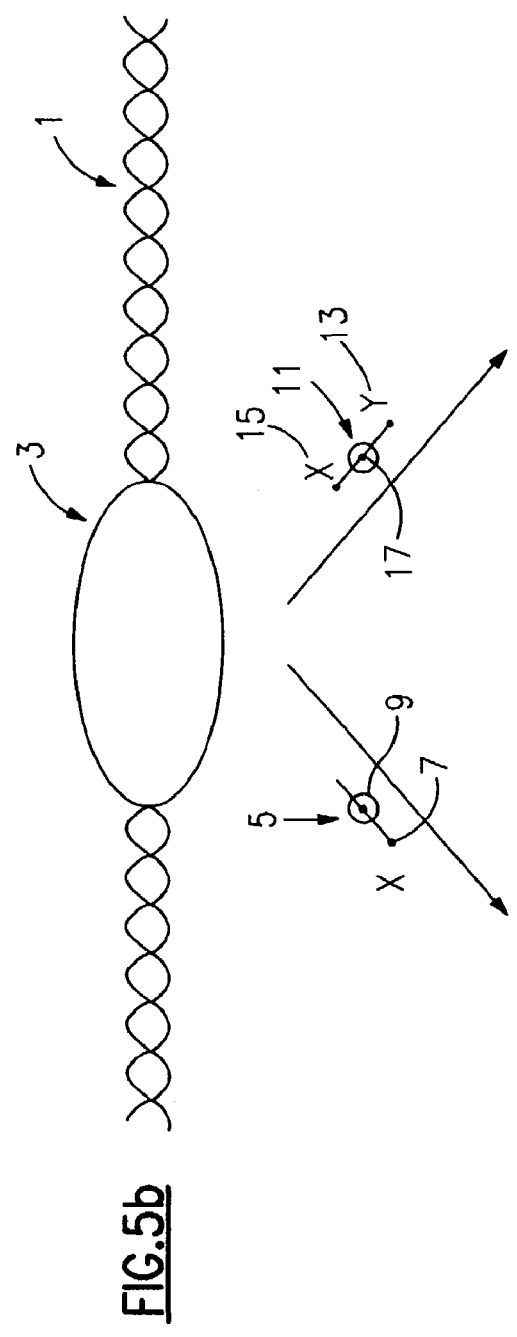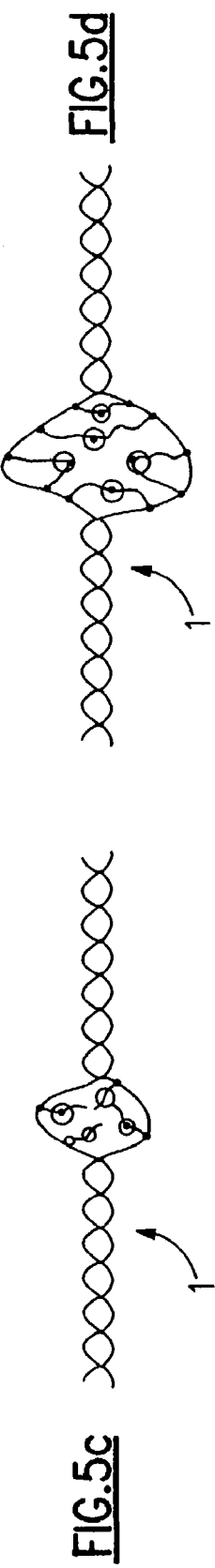
FIG.5a
FIG.5b
FIG.5c
FIG.5d

SYNTHESIS OF CHEMICAL TAGS

CROSS REFERENCE TO RELATED APPLICATION

The present application is a divisional application of Ser. No. 10/608,094, filed Jun. 30, 2003, now abandoned, which is a continuation of U.S. patent application Ser. No. 09/916,439, filed Jul. 30, 2001, which issued as U.S. Pat. No. 6,632,612 and is a continuation of U.S. patent application Ser. No. 09/668,140, filed Sep. 25, 2000, now abandoned, which is a continuation of U.S. patent application Ser. No. 09/154,584, filed Sep. 17, 1998, now abandoned, all of which are incorporated herein by reference in their entirety.

FIELD OF THE INVENTION

The present invention relates to methods for synthesizing chemical tags and structures that include the chemical tags.

BACKGROUND OF THE INVENTION

Chemical tags are utilized in a variety of applications. Typically, chemical tags are utilized for monitoring, analyzing, and controlling any number of parameters in a wide range of applications. For example, chemical tags can include one or more atoms and/or molecules that maybe detected through one or more techniques. For example, chemical tags can include radioactive isotopes. Such a chemical tag might be useful where simply the presence of the chemical tag needs to be detected. Chemical tags can also include materials that will fluoresce in response to irradiation by selected wavelengths of radiation. For example, some chemical tags may fluoresce in response to irradiation by ultraviolet radiation.

A variety of means typically are used to detect the presence of the chemical tags. For example, simple visual inspection can detect the presence of chemical tags that emit visible light, or fluoresce, in response to irradiation. In some cases, special films or detectors may be necessary to detect the presence of a chemical tag. For example, films or detectors sensitive to radiation produced by the tag may be utilized.

Chemical tags can be utilized in a variety of applications. Examples of these applications include pollution control, product identification, geological studies, detecting currents in oceans, uptake of materials by plants, among others.

SUMMARY OF THE INVENTION

Aspects of the present invention provide a method for forming a biological chemical tag. The method includes providing at least one double stranded DNA molecule. In the subsequent description, typically the DNA molecule is a double stranded DNA molecule. At least a portion of the at least one double stranded DNA molecule is denatured. At least one chemical moiety that prohibits recrystallization of the at least one denatured portion of the at least one, DNA molecule is attached to at least one nucleotide in the at least one denatured portion of the at least one DNA molecule.

Other aspects of the present invention provide a structure that includes at least one, DNA molecule that includes at least one denatured portion. The structure includes at least one chemical moiety attached to at least one portion of the at least one denatured portion of the at least one DNA molecule. The at least one chemical moiety prevents recrystallization of the at least one denatured portion of the at least one DNA molecule to which the at least one chemical moiety is attached.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the drawings and description are to be regarded as illustrative in nature and not as restrictive.

BRIEF DESCRIPTION OF THE DRAWINGS

The above-mentioned objects and advantages of the present invention will be more clearly understood when considered in conjunction with the accompanying drawings, in which:

FIG. 5a represents an embodiment of a DNA molecule that may be utilized in methods and structures according to the present invention;

FIG. 5b represents the embodiment of the DNA molecule illustrated in FIG. 5a including one denatured portion;

FIG. 5c represents the denatured portion of the embodiment of the DNA molecule illustrated in FIGS. 5a and 5b including an embodiment of a chemical tag according to the present invention;

FIG. 5d represents the denatured portion of the embodiment of the DNA molecule illustrated in FIGS. 5a and 5b including another embodiment of a chemical tag according to the present invention.

DETAILED DESCRIPTION OF THE INVENTION

Figure 1A:
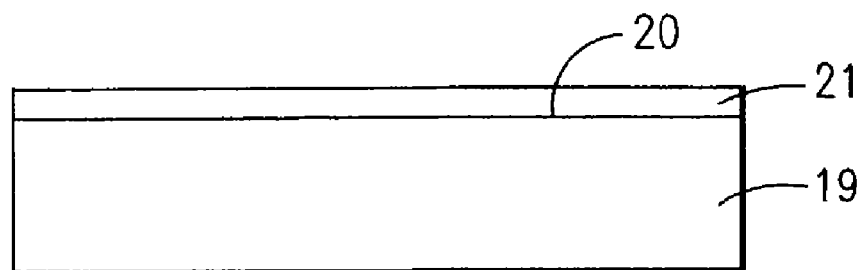
FIGS. 1a-1d represent cross-sectional views of an embodiment of a substrate that may be utilized according to one embodiment of the present invention at various stages of a method for producing the substrate according to the present invention.

As stated above, the present invention provides methods for synthesizing chemical tags. The present invention also includes a structure that incorporates at least one chemical tag according to the present invention. In particular, the present invention relates to chemical tags for DNA molecules.

According to the present invention, at least one DNA molecule is provided. The sequence of the at least one DNA molecule may or may not be known. Typically, the at least one DNA molecule is double stranded. At least one portion of the DNA molecule may be denatured. The denaturing may be carried out by exposing portions of the DNA molecule that it is desired to be denatured to a solution capable of denaturing DNA. Alternatively, additionally, the site or sites that it is desired to have denatured may be exposed to elevated temperatures.

In the event that a solution is utilized to denature the DNA, any solution capable of denaturing DNA may be utilized. The solution may have a high dielectric constant. The solution may include at least one salt. The salt may include at least one of NaCl, NaOH, Formamide, and Urea.

In the event that heat alternatively or additionally utilized, preferably, the DNA, at the sites that are to be denatured, is raised the temperature sufficient to result in the denaturing of the DNA molecule at those sites. For example, the DNA may be raised to a temperature of from about 70° C. to about 110° C.

After denaturing at least one portion of the DNA molecule, at least one chemical moiety, or insertion compound, may be attached to the DNA molecule in the at least one denatured portion of the DNA molecule. The at least one chemical moiety typically prohibits recrystallization of the at least one denatured portion to which the at least one chemical moiety is attached.

The chemical moiety may attach to a variety of different locations on the DNA molecule in a variety of different ways. For example, the at least one chemical moiety may hydrogen bond to one or more sites on the DNA molecule. Alternatively, covalent bonds may be formed between the at least one chemical moiety and at least one portion of the DNA molecule.

Furthermore, depending upon the nature of at least one chemical moiety, the location where the at least one chemical moiety attaches to the DNA molecule may vary. According to one example, the at least one chemical moiety may include at least one nucleotide that is complimentary to at least one nucleotide within a denatured portion of a DNA molecule. As such, the chemical moiety would hydrogen bond to a complimentary nucleotide on the DNA molecule similarly to how the nucleotide typically bond to each other in the double helix structure of the DNA. The at least one chemical moiety may include other atoms and/or molecules that may bond to the same or different site or sites as nucleotide would commonly bond to.

Alternatively, the at least one chemical moiety could include at least one acid group, such as a carboxylic acid, and/or at least one derivative of an acid group, such as a salt of a carboxylic acid. The acid groups can react with amine groups of the bases, to inhibit the DNA from recrystallizing or renaturing. Typical compounds may include an alkane chain with an acid group at its termination.

The at least one chemical moiety may include at least one portion that bonds to the denatured portion of the DNA molecule. However, the at least one chemical moiety may include more than one site that bonds to more than one site on the denatured DNA molecule. For example, the at least one chemical moiety could include two sites that bond to two sites on the denatured DNA molecule. For example, a long alkane chain with a nucleotide base at the two terminals.

The at least one chemical moiety, in addition to including at least one atom or molecule that bonds to the denatured portion of the DNA molecule may include a material that facilitates detection of the at least one chemical moiety. According to one example, at least one chemical moiety may include a luminous dye. The luminous dye may be chemically bonded to the at least one attachment portion of the chemical moiety. For example, it may be attached at one of the carbons of the alkane chain.

The at least one chemical moiety, or insertion compound, may be an oligomer that include a plurality of different chemical moieties connected together. The chemical moieties may include an attachment portion that assists in bonding the insertion compound to the DNA molecule. The insertion compound may also include a detection portion permitting the detection of the insertion compound.

The attachment portion of the insertion compound could include one or more nucleotide base. Insertion compound that bonds to more than one site on the DNA molecule could include an attachment portion at each end. For example, the insertion compound could include two nucleotides, one at each end. For example, an insertion compound could include guanine cytosine or thymine adenine. Any nucleotide base could be utilized at the ends of the insertion compound. According to one example of the present invention, the bases are complementary. According to another example, the bases are the same. A nucleotide base on the insertion compound can bond to a base on the denatured portion of the DNA molecule.

According to another example, the attachment portion of the insertion compound could include at least one acid, such as a carboxylic acid, or acid derivative, such as a salt of a carboxylic acid. Acids or acid derivative groups can react with amide groups of the bases, to inhibit them from recrystallizing or renaturing. According to one example, the insertion compound includes an acid at one end. Other attachment groups could include acid chloride, isocyanate, phosphonic dichloride.

As stated above, the attachment group or groups may be bonded to a detection group. The detection group utilized may depend on how it is desired that the insertion compounds be detectable. For example, the insertion compound could include a dye. The dye could be luminescent under irradiation.

If the insertion compound is a luminescent dye, the dye compound may first be formed. According to one example, the luminescent dye includes a polymeric chain with at least one functional group to which a dye may be attached. The polymeric chain could include any desired polymer. Examples of polymers that may be utilized in the insertion compound include

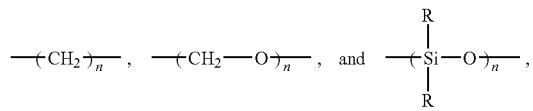

wherein $2 \leq n \leq 1000$; $R = CH_3$; $C_2H_5$;

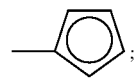

aromatic or aliphatic hydrocarbons having less than 30 carbon atoms; or any inert group including carbon and hydrogen. The functional group, defined as "x", may include

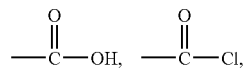

$NH_2$, —OH or any other Lewis acid or Lewis base.

The at least one functional group, to which the dye may be attached, may be attached to the polymer chain at various locations. For example, the functional group may be attached at the end of the polymer chain. According to another embodiment, the functional group may be attached to the polymer chain anywhere between the ends of the polymer chain. For example, the functional group could be attached in the vicinity of the middle of the polymer chain.

After formation of the polymer chain and attachment of the functional group(s), at least one dye molecule may be attached to the functional group. Dyes that may be utilized according to the present invention include naphthalene-based dyes, anthracene-based dyes, fluorescein-based dyes, and rhodamine-based dyes. The following present examples of such dyes that may be utilized according to the present invention:

Naphthalene-Based Dye

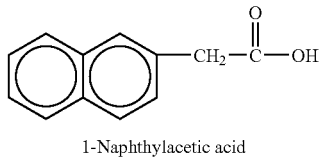

1-Naphthylacetic acid

Functional groups that may be utilized with this dye include —OH and —NH$_2$;

Anthracene-Based Dye

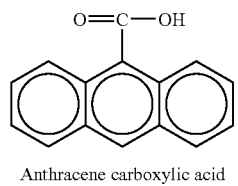

Anthracene carboxylic acid

Functional groups that may be utilized with this dye include —OH and —NH$_2$;

Fluorescein-based Dye

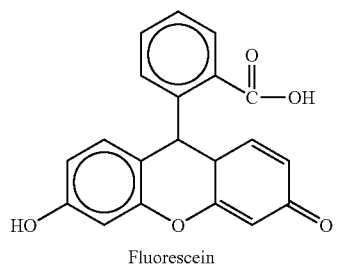

Fluorescein

Functional groups that may be utilized with this dye include —OH and —NH$_2$; and Rhodamine-based Dye

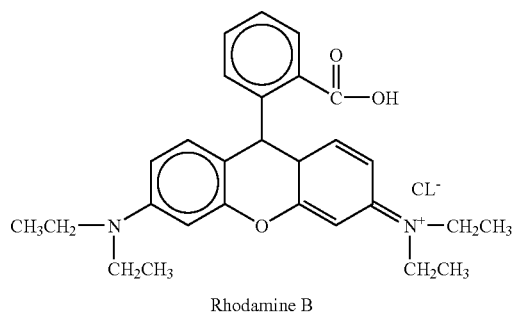

Rhodamine B

Functional groups that may be utilized with this dye include —OH and —NH$_2$.

FIG. 5a illustrates an embodiment of a DNA molecule that could be utilized according to the present invention. FIG. 5b illustrates the embodiment of the DNA molecule illustrated in FIG. 5a wherein one portion of the DNA molecule has been denatured. FIGS. 5c and 5d illustrate two embodiments of the present invention wherein insertion compounds have been bonded to the denatured portion 3.

For example, FIG. 5c illustrates an embodiment wherein four insertion compounds have been bonded to the denatured region 3 of the DNA molecule 1. Each insertion compound 5 includes one attachment portion 7 and one detection portion 9. Four insertion compounds have been bonded to the denatured portion 3 of the DNA molecule illustrated in FIG. 5c.

On the other hand, in the embodiment illustrated in FIG. 5d, five insertion compounds have bonded to the denatured region. Each insertion compound in the embodiment illustrated in FIG. 5d includes attachment portions 13 and 15 and a detection portion 17. As can be seen in FIG. 5d, each insertion compound is bonded to two sites on the denatured region of the DNA molecule.

The denaturing of the DNA may be facilitated by arranging the DNA on a substrate prior to denaturing at least a portion of the DNA molecule. The substrate provided according to the present invention may include at least one region wherein when the DNA is arranged adjacent to this region it will be denatured. The at least one region of the substrate where the DNA is denatured when arranged adjacent to it may include properties that result in retaining a solution that causes the DNA to denature. For example, the at least one region of the substrate may have a particular wetting property that causes the solution to be retained on the portion.

To facilitate differential retention of the solution on the substrate, the substrate may be provided with regions having different wetting properties. These regions having different wetting properties may be provided in a plurality of lines. The areas having different wetting properties may have a plurality of different wetting properties. Typically, the substrate includes areas having two different wetting properties. In a substrate that includes regions having two different wetting properties, preferably, one of the wetting properties results in retention of the solution that can denature a DNA molecule ranged thereon while the other region does not tend to retain the solution.

The regions having different wetting properties may be provided in a plurality of alternating lines wherein each line of one wetting property on each side. The lines may all have the same width. Alternatively, all the lines of one wetting property may have one width while all the lines of another wetting property may have a different width. However, any number of lines having any number of wetting properties may be provided with a variety of widths.

According to one embodiment, the substrate includes two different types of lines having two different types of wetting properties. According to this embodiment, the lines of the first type have a width of about 10 nm to about 1000 nm. Also according to this embodiment, the lines of the second wetting type have a width of about 10 nm to about 10000 nm. Furthermore, according to this embodiment, the lines of the first type, have a width of from about 10 nm to about 1000 nm tend to retain the solution capable of denaturing DNA arranged on the substrate.

All the lines of one type may tend to retain denaturing solution, while all the lines of the other type tend to not retain the denaturing solution. Additionally, all the lines of one wetting property type may have one width and all the lines of the other wetting property type may have another width. The two widths may or may not be the same. For example, all the lines of one wetting type may be provided with a width that is less than the other, such that all of the lines of one type are wider that all of the lines of the other type. Alternatively, all the lines of both types could have the same width.

Rather than providing regions on a substrate that have different wetting properties, the substrate may include at least one channel for retaining the denaturing solution. The substrate may include a plurality of channels in the substrate. The size of the channels may depend upon the size of the region of the DNA molecule arranged on the channels that it is desired to denature. Further, the number of channels may depend upon the length of the DNA molecule that is to include the at least one denatured portion.

According to another embodiment, the at least one portion include at least one channel for retaining the solution. A solution may be deposited on the substrate such that it will be arranged at least on the at least one portion of the substrate where the solution is such that at least a portion of the DNA will be denatured when being arranged on the substrate.

According to one embodiment, each channel in the substrate has a depth of about 10 nm to about 500 nm. The depth can be measured as the depth of the deepest part of a channel with respect to the surface of the substrate. If the substrate includes a plurality of channels, each channel may have substantially the same depth. Alternatively, the channels may have different depths.

The at least one channel provided in a substrate may also have a width of about 10 nm to about 10000 nm. If the substrate includes a plurality of channels, each channel may have substantially the same width. Alternatively, the channels may have different widths.

The width of the channels may refer to the width of the opening of the channels. The width of the opening of the channel may be measured from the surface of the substrate where the channel first begins or from a portion of the opening of the channel further width of the channel. The minimum width of the channels may be from about 10 nm to about 10000 nm.

The width of the channels or the opening of the channels or, alternatively, the width of portions of a substrate having a wetting property that tends to retain a denaturing solutions in embodiments that do not include channels may have a sufficient depth and width in the case of channels or sufficient width, in the case of a surface having various wetting properties, to accommodate an amount of solution sufficient to result in a selected amount of contact between the solution and at least one DNA molecule arranged on the portion of the substrate where the solution is located to result in a selected amount of denaturing the at least one DNA molecule. Also, the width and/or depth of the channels or regions may be sufficient to retain a desired amount of denaturing solution to result in denaturing a certain amount of a DNA molecule.

The channels may be separated from each other by a distance of about 10 nm to about 1000 nm. This separation may be measured from the edge of the opening of one channel to the adjacent edge of the opening of an adjacent channel. Alternatively, the separation could be measured from the center line of one channel to the center line of an adjacent channel.

The channels or the regions of the substrate having a wetting property that tends to retain denaturing solution may be separated by regions of the substrate. The separating regions may have characteristics that make them tend to retain DNA molecules that contact them. Along these lines, the separating regions may have a width sufficient to result in a selected degree of retention of a DNA molecule arranged on the substrate. The number of base pairs over the channel that may denature may range from about 40 to about 40,000. This number of base pairs corresponds to a width of about 10 nm to about 10,000 nm.

After providing channels in the substrate, a solution may be deposited on at least a portion of the substrate including at least one of the channels. The solution includes the denaturing solution described above.

The solution can be deposited over the entire substrate or only over portions of the substrate. The denaturing solution may be an aqueous solution. The solution may have a high dielectric constant. Additionally, the solution may include at least one salt. Examples of salts include NaCl, NaOH, Formamide, and urea. The solution may include at least one polar solvent. One example of a polar solvent is water.

If the substrate includes regions that do not tend to retain the solution, they may tend to repel the solution or just tend not retain the solution. If the portions of the substrate tend not to retain the solution or repel the solution, they may tend to retain at least a portion of the DNA molecule arranged on that portion of the substrate. As such, the surface between the channels may be considered a dewetting surface. The DNA typically is in physical contact with the surface of the substrate between the channels and interact with it by at least van der Waals' forces. These regions that tend to retain the DNA may be only slightly hydrophilic.

After deposition of the denaturing solution on the substrate, whether the substrate includes channels or regions having different wetting properties, any excess solution may be removed. Whether or not the solution needs to removed depends upon whether the proper amount of solution is deposited such that the solution is substantially confined to desired portions of the channels and/or regions having the desired wetting characteristics. Typically, it is desirable to control where the solution is deposited on the substrate so that it is possible to control where DNA deposited on the substrate and the solution is denatured.

After deposition of denaturing solution in selected areas of the substrate, at least one DNA molecule may be arranged on the substrate. Typically, the at least one DNA molecule is arranged on the substrate such that it will contact a plurality of areas where the denaturing solution has been deposited as well as a plurality of areas where the denaturing solution has not been deposited.

Additionally, a plurality of DNA molecules may be arranged on one substrate. For example, from about 2 to about 10,000 DNA molecules may be arranged on the substrate. To arrange the DNA molecules on the substrate, first a DNA containing solution may be deposited on the substrate. Preferably, the size of DNA molecules is larger than the channel width so that the DNA does not fully fall inside the channel.

The solvent, such as $H_2O$, may then be evaporated. Then, the denaturing fluid is injected in the channel from one end of the substrate. This denaturing fluid is wicked into the channels by surface tension.

After deposition, the DNA molecules typically are permitted to sit or dwell on the substrate for a period of time sufficient to permit the desired amount of denaturing of the DNA molecule to occur. For example, typically, after the solution is injected, the DNA molecules may be permitted to denature for about 1 minute to about 60 minutes.

After a sufficient amount of time has passed for a desired amount of denaturing of the DNA molecule to occur, the insertion compound may be deposited on the substrate and DNA arranged on the substrate. The insertion compound may be substantially as described above. The insertion compound may be applied to the denatured DNA on the substrate by including; the insertion compound in the denaturing solution.

After denaturing, the insertion compound may then be permitted to attach to the denatured portion or portions of the DNA molecule. By knowing the sequence of the DNA molecule deposited on the substrate and the makeup of the insertion compound, the locations where the insertion compound will attach to the DNA molecule may be controlled. On the other hand, where the sequence of the DNA is unknown, the insertion compound may attach in unknown locations, permitting the sequence to be determined as described below.

After a sufficient time has passed for the insertion compound(s) to bond to the DNA molecule(s) arranged on the substrate, excess insertion compound(s) may be removed from the vicinity of the DNA molecule(s). Excess insertion compound may be any insertion compound not attached to a denatured portion of a DNA molecule. For example, the excess insertion compound(s) may simply be washed away.

After attachment of one or more insertion compounds to one or more denatured portions of one or more DNA molecules, the location(s) of the insertion compound(s) on the DNA molecule(s) may be detected. In the case where the insertion compound includes a luminescent dye, such as a fluorescent dye, the DNA molecule and attachment insertion compounds may be irradiated with a wavelength of light that caused the dyes to fluoresce. Hence, the location of the DNA may be defected.

Additionally, the portion of a DNA molecule that includes the at least one denatured section could be considered a "writable segment". If the DNA molecule is arranged on a substrate, the portion of the DNA molecule arranged in the substrate could be considered the "writable segment". According to such analysis, locations where an insertion compound is attached to a denatured portion of the DNA molecule could be assigned a value of one (1). Similarly, if a denatured portion of the DNA does not include an insertion compound, that location of the DNA could be assigned a value of zero (0).

Portions of the denatured DNA molecule could be locally "written" with 1's and 0's utilizing different solutions in different channels of the DNA molecule. Thus, the DNA strand could be modified by 1's and 0's. This would essentially lead to a molecular bar code that may be read utilizing optical methods and apparatus, such as a optical detector.

According to one embodiment, each channel or region of the substrate having a wetting property such that the region tends to retain the denaturing solution has a width of about 100 nm. According to this embodiment, the channels or regions having the denaturing solution retaining wetting property are separated by about 1000 nm. Also, the portion of the substrate including the channels or particular regions has a width of about 10 mm. If a strand of DNA at least 10 mm long were arranged over the substrate, about 10000 denatured portions of the DNA strand can be "written" given the above-described parameters of the substrate. Having 10000 writable segments could lead to identification of $2^{10000}$.

The denaturing of the DNA could also be carried out or facilitated by heating the DNA in locations where it is desired that the DNA be denatured. If the DNA is arranged on a substrate, the heating may be accomplished by providing the substrate with heatable portions. The heatable portions could be provided in a substrate in place of or in addition to the channels and/or regions having certain wetting properties. Additionally, it is not necessary for the heatable portions to be provided in and/or on a substrate.

According to one embodiment, the heatable portions of the substrate are provided by metal arranged in and/or on a substrate. The metal may be heated by passing a current through the metal much as a resistive heating element in a stove heats up by passing a current through it.

The current may be provided continuously, and/or periodically. According to one example, the current is pulsed. The pulsing may be regularly or irregularly timed. The current could be a combination of continuous and pulsed current. A structure including such wires is described below in greater detail. The local temperature may range from about 70° C. to about 110° C. The elevated temperature may be applied in pulses or continuously. If the temperature is applied in pulses, the pulse time period that the elevated temperature is applied may be at least about 100 ns.

As stated above, according to the present invention, DNA may be arranged on a substrate. Typically, the substrate has a smooth upper surface. The substrate may include a plurality of channels or regions having different wetting properties. The channels or regions may be provided in lines. The lines may have a width $l_1$. A region or "land" of the substrate may be provided between the channels or regions. The "land" may have a width 12. Thus, the pitch between the lines or regions may be described as $l_1 + l_2$. If the substrate includes channels, the channels may have a depth d.

If the denaturing solution is water or an aqueous solution, the channels or regions may have a width of from about 10 nm to about 1000 nm and may be separated by "lands" such that $l_2$ is about 10 nm to about 10000 nm. The depth of the channels from about 10 nm to about 500 nm.

A substrate according to the present invention may be fabricated according to a plurality of methods. FIGS. 1a-1d illustrate one embodiment of a substrate at various stages throughout one embodiment of a method according to the present invention. According to the embodiment of the method illustrated in FIGS. 1a-1d, a substrate 19 is provide. The substrate may be a semiconductor material. For example, the substrate could be silicon.

A surface 20 of substrate 19 may be treated with a material to make it only partially hydrophilic. For example, the contact angle could be about 10° to about 40°. According to one example, the surface may be treated with weak HF to make it hydrophilic. "Weak" HF could include about 1 part HF in about 100 parts $H_2O$.

Other treatments may be utilized to make the surface of the substrate hydrophilic. For example, the surface could be treated with an alkaline solution. Examples of alkaline solutions that could be utilized include solutions of $NH_4OH$ and NaOH.

After treating the surface 20 of the substrate 19 to make it only partially hydrophilic, new layer of at least one photoresist 21 may be deposited on the surface of the substrate that has been made partially hydrophilic. Any photoresist material may be used in this case. Although any number of photoresists may be utilized, according to one embodiment, it is preferred that the photoresist has a high silicon content so that it may act as an etch stop during plasma processing in later steps. However, any standard photoresist may be utilized. For example, any photoresist that may be imaged by UV to deep UV light ($\lambda$=about 190–about 410 nm) could be utilized. Also, resist imagable by electron beam may be used. One such resist is PMMA.

After deposition of the layer of photoresist 21, the photoresist(s) may be selectively exposed to wavelengths of radiation that it is sensitive to. According to one embodiment, the photoresist is exposed in a pattern that corresponds to the pattern of channels that are to be formed in the substrate. In other words, the photoresist may be exposed to form an image corresponding to the line widths and line pitch that it is desired to form in the substrate.

Figure 1B:
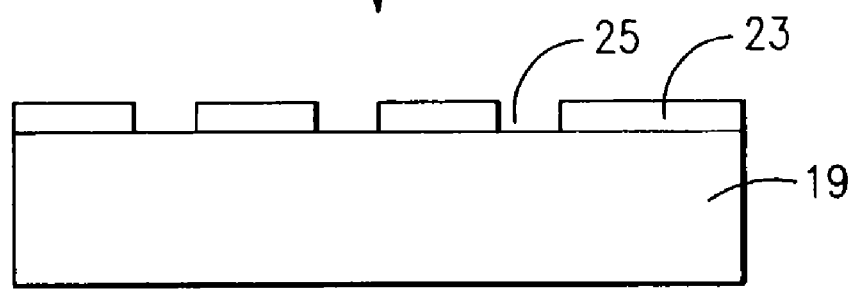
Figure 1C:
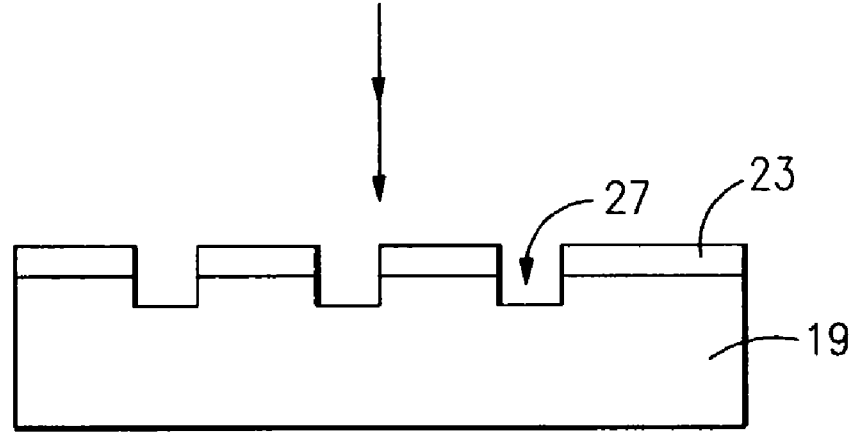

After exposure, the photoresist may be developed to selectively remove portions of the photoresist to result in the structure illustrated in FIG. 1b. As illustrated in FIG. 1b, the structure now includes a plurality of regions 25 where the photoresist has been removed and a plurality of regions 23 where the photoresist remains.

After exposing and developing the photoresist, the substrate 19 may be further treated to form the channels in the substrate. The channels may be formed utilizing a variety of processes. For example, reactive ion etch (RIE) may be used to etch the substrate 19 in the regions 25 exposed by removal of the photoresist. In other words, the remaining photoresist acts as a mask for removal of portions of the substrate 19.

The etching of the substrate 19 may be anisotropic. An anisotropic etch may result in good trench definition. The etching may be carried utilizing a $Cl_2$, low pressure plasma. Other etching treatments may also be utilized. For example, a plasma including $NF_3$ and at least one hydrocarbon could be utilized. The hydrocarbons utilized in the plasma could include any aliphatic or aromatic hydrocarbon with from 1 to about 20 carbon atoms. Alternatively, etching could include utilizing an $SF_6$ plasma at about $-100°$ C. Furthermore, etching could involved a 10% $H_2/CF_4$ reactive ion etch.

The etching may be carried out until a desired amount of the substrate 19 has been removed to result in channels of a desired depth. The depths may be as described above. One skilled in the art would understand how long to carry out the etch to result in trenches of a selected depth.

The channels 27 may be provided in the substrate such that they are all parallel. Alternatively, the channels may not all be parallel. For example, the substrate could include some channels that are perpendicular to others.

After formation of the trenches, the surface of the substrate in the trenches 27 may be exposed to one or more materials to make the surface of the substrate within trenches hydrophilic. The surface of the substrate within the trenches may be treated to be more hydrophilic than the surface of the substrate still covered by the photoresist. For example, the substrate could be treated such that the contact angle with respect to $H_2O$ should be less than about 15°.

According to one example, the exposed substrate within the trenches may be subjected to a water plasma to make the surface hydrophilic. In general, any plasma that forms —OH groups at the surface may be utilized.

Figure 1D:
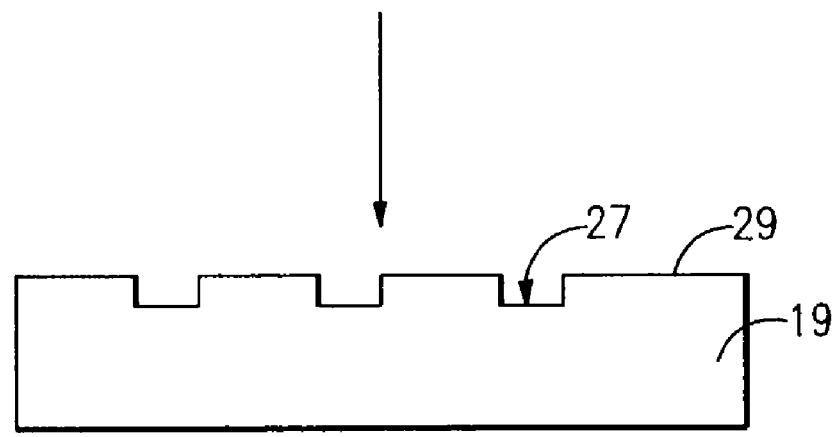

After making the surface of the substrate within the trenches hydrophilic, the remaining photoresist portions 23 may be removed from the substrate 19. The remaining photoresist may be stripped utilizing any suitable known method. A resulting structure is illustrated in FIG. 1d. This structure includes trenches 27 and lands 29. As described in the above treatment, the lands 29 may be slightly hydrophilic and the trenches 27 may be strongly hydrophilic.

FIGS. 2a-2d represent various stages of substrate during another embodiment of a process according to the present invention for forming the substrate on which at least one DNA molecule is to be denatured. According to the method illustrated in FIGS. 2a-2d, a substrate 31 is provided. A substrate may be a semiconductor material. For example, the substrate could be a silicon wafer. The silicon wafer could be a <100>, n-doped silicon wafer. The substrate may have a resistivity of about 2 to about 5Ωcm.

Next, a layer of a dielectric material 33 may be deposited on a surface of the substrate 31. Any suitable dielectric material may be utilized. For example, the dielectric layer may be an oxide or a nitride. Examples of oxides and nitrides include $Si_3N_4$ or $SiO_2$. Other materials other than dielectrics could be utilized. For example at least one metal could be utilized. However, metals may not etch as selectively.

After depositing the layer of dielectric material, a layer of a photoresist 35 may be deposited on the layer of the dielectric material 33. Any suitable photoresist material may be utilized. According to one embodiment, it is preferred that the photoresist has a high silicon content so that it may act as an etch stop during plasma processing in later steps.

However, any standard photoresist may be utilized. For example, any photoresist that may be imaged by UV to deep UV light ($\lambda$=about 190–about 410 nm) could be utilized. Also, resist imagable by electron beam may be used. One such resist is PMMA.

The photoresist may be applied in any known manner. For example, the photoresist may be spin cast on the layer of dielectric material 33.

Figure 2A:
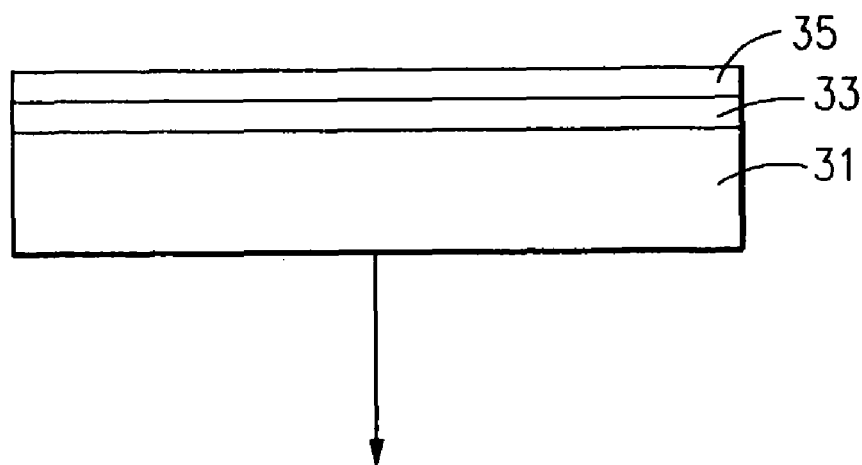
FIGS. 2a-2d represent cross-sectional views of another embodiment of a substrate that may be utilized according to one embodiment of the present invention at various stages of a method for producing the substrate according to the present invention.
Figure 2B:
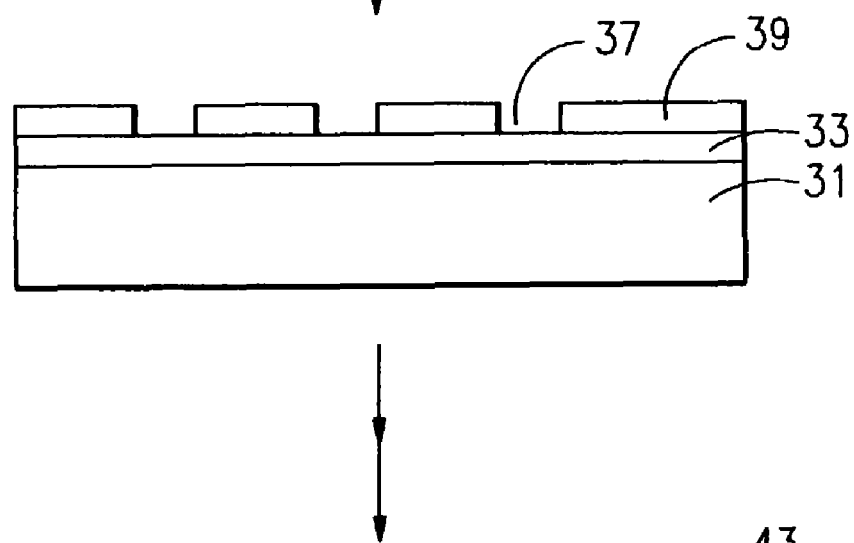

After depositing the layer of photoresist, it may be exposed and developed similarly to the process described above with respect to FIGS. 1a-1d. Selective removal of the photoresist as a result of development results in a structure as illustrated in FIG. 2b, similar to the structure shown in FIG. 1b. Accordingly, the structure illustrated in FIG. 2b includes substrate 31, dielectric layer 33, and photoresist layer that has been patterned to include openings 37 and regions 39 where the substrate remains.

Utilizing the photoresist as a mask, similar to the process described above and showed in FIGS. 1a-1d, the dielectric layer 33 may be etched. Etching of the dielectric layer may be carried out utilizing any suitable process and/or material. For example, the dielectric material may be etched utilizing using a wet etch chemistry. According to one example, HF is utilized to etch the dielectric layer. Alternatively, a reactive ion etch may be utilized. The reactive ion etch may utilize a plasma.

Figure 2C:
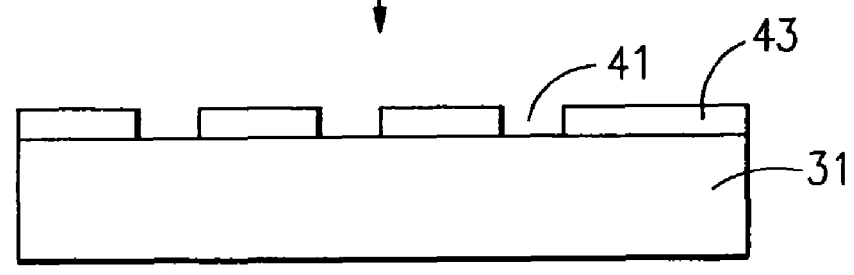

Etching the dielectric layer 33 results in the formation of openings 41 therein and remaining regions 43 adjacent the openings. After etching of the dielectric layer, the remaining photoresist regions 39 may be removed. Stripping or removing the remaining photoresist regions 39 may be carried out according to any suitable known process. FIG. 2c illustrates the structure after removal of the remaining photoresist.

After removal of the remaining photoresist, the substrate 31 may be etched. The etching is carried to create channels in the substrate. In the embodiment illustrated in FIG. 2d, the channels are etched so that they undercut the dielectric material 43. However, it is not necessary that the channels undercut the dielectric material 43.

Etching of the substrate 31 may be carried according to any known etching process. For example, the substrate 31 may be isotopically etched. The etching could be carried with a plasma, such as a $CF_4$ plasma, a 3:1 $SF_6/O_6$ RIE plasma, or a $Cl_2/CClF_3$, $CClF_3$>50% plasma.

After creating channels 45 in the substrate 31, the surface of the substrate within the channels may be exposed to a material to make them hydrophilic. The material that the surface of the substrate within channels is exposed to could include sulfuric acid and/or hydrogen peroxide. These materials may make the surface strongly hydrophilic. Rendering the surface of the channels hydrophilic may be carried out by soaking only the channels in the solution.

While the surface of the channels may be hydrophilic, the surface of the dielectric material 43 remaining on the surface of the substrate 31 may be less hydrophilic. In fact, the surface of the dielectric may be only slightly hydrophilic. The resulting structure as illustrated in FIG. 2d.

Figure 2D:
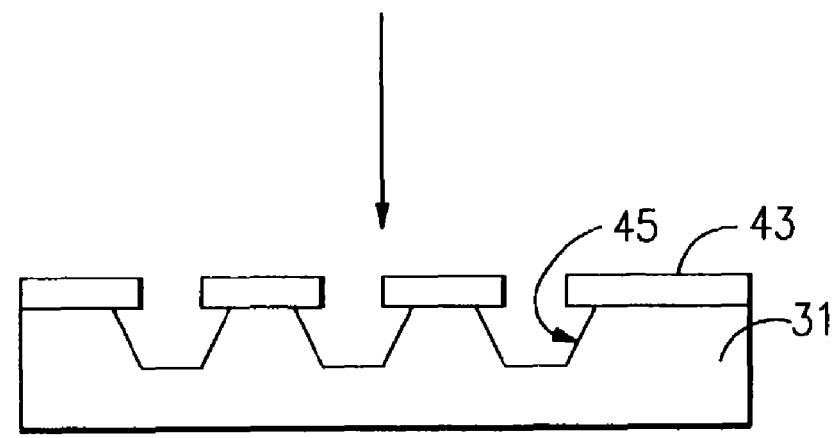
Figure 3A:
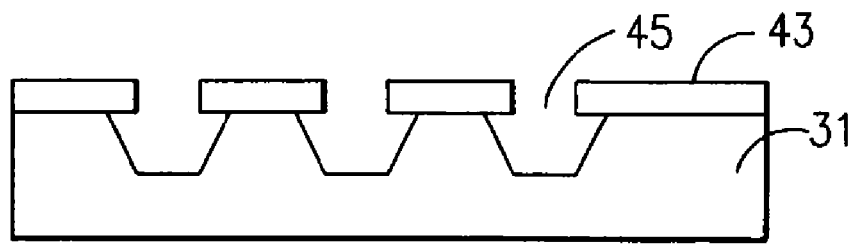
FIGS. 3a-3c represent cross-sectional views of an additional embodiment of a substrate that may be utilized according to one embodiment of the present invention at various stages of a method for producing the substrate according to the present invention.
Figure 3B:
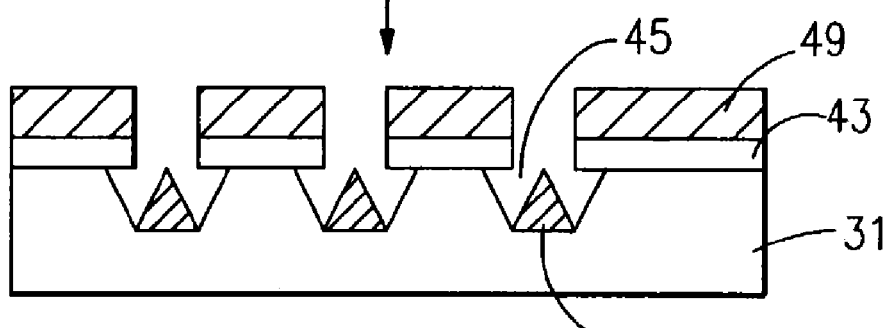
Figure 3C:
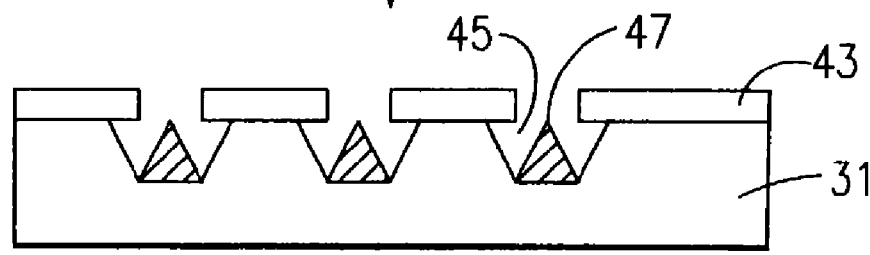

The structure illustrated in FIG. 2d may be further processed to provide structure for heating DNA arranged over the channels. FIGS. 3a-3c illustrate an embodiment of a substrate according to the present invention at various stages of a process according to the present invention for providing the substrate with means to raise the temperature of the DNA molecules arranged thereon.

The structure illustrated in FIG. 3a corresponds to the structure illustrated in FIG. 2d. One or more metals and/or alloys may be deposited on the structure in FIG. 3a. The metal could include at least one noble metal. For example, gold could be deposited on the structure illustrated in FIG. 3a. The gold or other metal could be deposited by any known process. For example, a standard sputtering process could be utilized.

FIG. 3b illustrates a structure where metal has been deposited on the structure illustrated in FIG. 3a. The structure illustrated in FIG. 3b includes metal 47 deposited within channels 45 and metal 49 deposited on dielectric portions 43. The metal 47 deposited in the channels 45 may have a conical cross-section as illustrated in FIG. 3b. The metal may be deposited on at least a portion of the surface of the dielectric portions 43 as well at least a portion of the surface of the channels 45. The conical cross section may be formed by a simple shadowing effect as the metal passes through the opening of the channel.

After deposition of the at least one metal on at least a portion of the surface of the channels and/or the dielectric regions 43, selected portions of the metal may be removed. According to one embodiment, all of the metal 49 on the dielectric 43 may be removed. At least a portion of the metal 47 within the channels 45 may or may not also be removed at the same time.

Removal of the metal may be carried out according to any known process. According to one embodiment of the present invention, the metal is removed by exposing the substrate and the metal deposited thereon to at least one liquid metal. Liquid metals have high surface energy and therefore may tend not to go into the channels and remove the metal within the channels. The liquid metal could be mercury and/or gallium. After selected removal of the metal, the structure illustrated in FIG. 3c results.

The structure illustrated in FIG. 3c may be utilized to apply heat to DNA molecules arranged on a substrate to denature the DNA in the vicinity of the deposited metal. Current may be passed through the metal 47 in the channels 45 to cause the DNA to denature in the vicinity of the metal. The heating may be carried out in addition to and/or instead of utilizing a denaturing solution.

Rather than providing channels in a substrate wherein a denaturing solution is deposited within the channels, the present invention may include a substrate that includes a grating that includes slits formed completely through the substrate. The substrate including the grating may arranged over a reservoir of denaturing solution and the DNA arranged on the substrate.

FIGS. 4a-4e illustrate an embodiment of a substrate at various stages of an embodiment of a process that may be utilized for forming a grating in the substrate. According to this process, a multi-layer substrate may be provided. The substrate may include a core 51 of a semiconductor material. The semiconductor material may be a silicon wafer. According to one example, the silicon wafer is a <100> silicon wafer.

At least one layer of a dielectric material may be provided on a top surface and a bottom surface of core 51. While the layers of dielectric material 53 and 55 may be the same dielectric material. Alternatively, the layers of dielectric material 53 and 55 may be different. By providing different dielectric materials on the top and bottom surfaces of the core 51, the layers of dielectric material may be differentially treated. According to one embodiment, the layers of dielectric material 53 and 55 may include a nitride and/or an oxide. The oxide and/or nitride could be based on the underlying semiconductor core. For example, the dielectric material could include $SiO_2$ and/or $Si_3N_4$.

The multi-layer substrate may also include at least one layer of photoresist deposited on each layer of dielectric material. The structure illustrated in FIG. 4a includes layers of photoresist 57 and 59 deposited on layers of dielectric material 53 and 55. As with the dielectric material, the same photoresist may be deposited on the dielectric material. Alternatively, each layer of photoresist may include a different composition.

Any suitable photoresist material may be utilized. According to one embodiment, it is preferred that the photoresist has a high silicon content so that it may act as an etch stop during plasma processing in later steps. However, any standard photoresist may be utilized. For example, any photoresist that may be imaged by UV to deep UV light ($\lambda$=about 190–about 410 nm) could be utilized. Also, resist imagable by electron beam may be used. One such resist is PMMA.

Also, any suitable dielectric material may be utilized. For example, the dielectric layer may be an oxide or a nitride. Examples of oxides and nitrides include $Si_3N_4$ or $SiO_2$. Other materials other than dielectrics could be utilized. For example at least one metal could be utilized. However, metals may not etch as selectively.

Figure 4A:
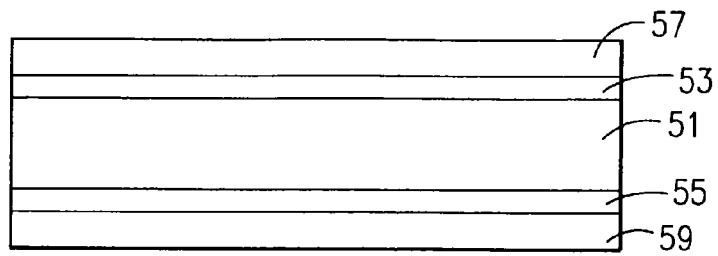
FIGS. 4a-4e represent cross-sectional views of an further embodiment of a substrate that may be utilized according to one embodiment of the present invention at various stages of a method for producing the substrate according to the present invention.

FIG. 4a illustrates one embodiment of a multi-layer substrate according to the present invention. After providing the multi-layer substrate illustrated in FIG. 4a, the photoresist layers 57 and 59 may be selectively exposed to wavelengths of radiation that they are sensitive to. Typically, one of the layers of photoresists is exposed in a pattern such that when developed, portions of the photoresist(s) that are removed by the developing form a pattern corresponding to width and pitch of slits that are formed the grating that the DNA will be arranged on. Additionally, typically, the other layer of photoresist is exposed so as to produce an opening corresponding to an opening that is to be etched in the underlying dielectric and/or core that solution may enter from a solution reservoir that the grating is placed over.

Figure 4B:
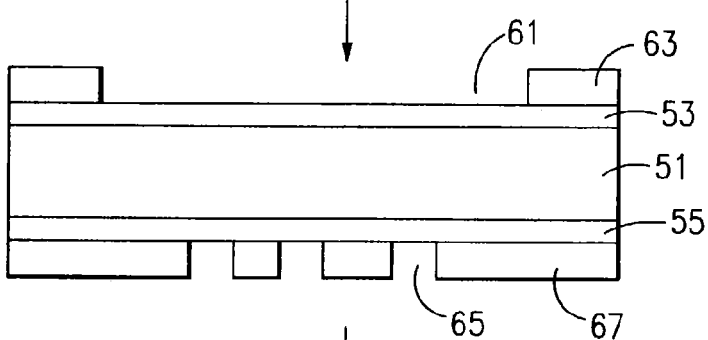

After development, the photoresist layers may be developed. FIG. 4b illustrates an embodiment of a structure according to the present invention where the photoresist has been developed. Development of the photoresist may result in openings 61 and 65 and remaining portions 63 and 67. Openings 65 in the embodiment illustrated in FIG. 4b represent the slits that will form the grating that the DNA is arranged over.

After developing the photoresist, the underlying layers of dielectric material may be etched utilizing the remaining photoresist as a mask. The dielectric materials may be etched utilizing any applicable process. For example, if dielectric layer $SiO_2$, reactive ion etch may be utilized. The reactive ion etch may be carried out with a plasma that includes $C_2F_6$/$CHF_3$ and $SF_6$/$O_2$. Other processes and/or process parameters may also be utilized to etch a different dielectric material. For example, if the dielectric material $Si_3N_4$, a reactive ion etch plasma including $CF_4$/$O_2$ may be utilized.

After etching the dielectric layers, to help ensure that all dielectric material is removed from the spaces defined by opening 61 and 65 in the photoresist, the surface of the core 51 may be cleaned to remove any dielectric residues. For example, any suitable cleaning method and material may be utilized. According to one example, HF is utilized to ensure removal of the dielectric residue.

Figure 4C:
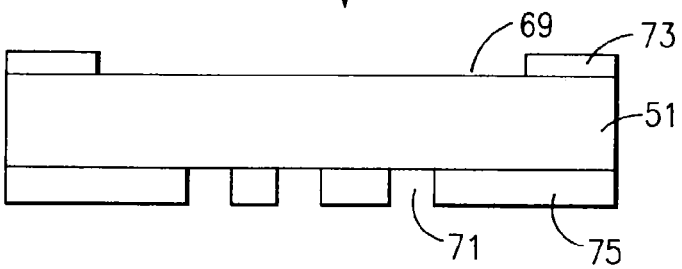

After removal of any dielectric residue, any remaining portions of the photoresist, 63 and 67, may be removed from the multi-layer structure. FIG. 4c illustrates the resulting structure. As can be seen in the embodiment illustrated in FIG. 4c, openings 69 and 71 have been formed in the layers of dielectric material 53 and 55. Portions 73 and 75 of the layers of dielectric material may also remain on the core 51 of the multi-layer substrate.

After removal of the remaining photoresist, the core 51 of the multi-layer structure may be etched utilizing the remaining dielectric portions as a mask. First, one side of the core structure may be etched. First etching of the core 51 may be anisotropically etched in a KOH solution.

Figure 4D:
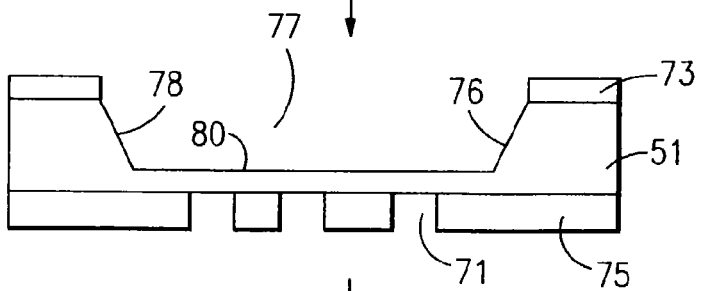

FIG. 4d illustrates a resulting structure. The structure illustrated in FIG. 4d includes a large opening 77 that has been etched in core 51. This opening 77 is the opening that will be placed adjacent a denaturing fluid reservoir. The surfaces 76 and 78 may be (111) silicon.

Initially, the top surface of core 51 may be (100) plane. During etching, the (100) plane etches at a faster rate than (111) plane. As a result, a trench 77 may be obtained with surface 80 being (100) and the side walls 76 and 78 being (111).

After etching one side of the core layer 51, the opposite side may be etched. This etch may be carried out as described above with respect to the processes illustrated in FIGS. 1a-1d and FIGS. 2a-2d where the substrate was etched to form channels in the substrate.

After etching the slits 79 in the core and layer 51, the remaining portions of dielectric layers 75 may be removed. Any suitable method and/or material may be utilized to remove the dielectric layer portions 75 remaining on the core 51. For example, if the dielectric material is a nitride, such as $Si_3N_4$, phosphoric acid may be utilized to remove the remaining portions of a dielectric material. If phosphoric acid is utilized to remove the dielectric material 75, at 85% solution of phosphoric acid at about 180° may be utilized. Alternatively, the dielectric material layer portions 75 may be removed with reactive ion etching. According to one embodiment, $CF_4/O_2$ may be utilized.

Figure 4E:
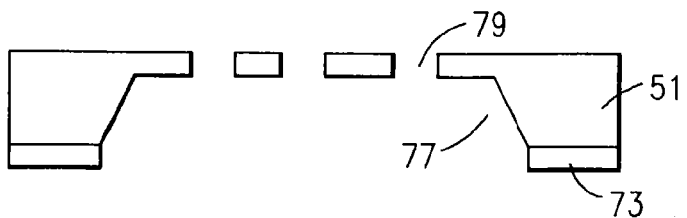

FIG. 4e illustrates the structure resulting from removal of dielectric layer portions 75.

After formation of a structure such as that illustrated in FIG. 4e, the structure may be arranged adjacent a reservoir filled with a denaturing solution. The DNA may then be arranged on the structure.

Figure 6:
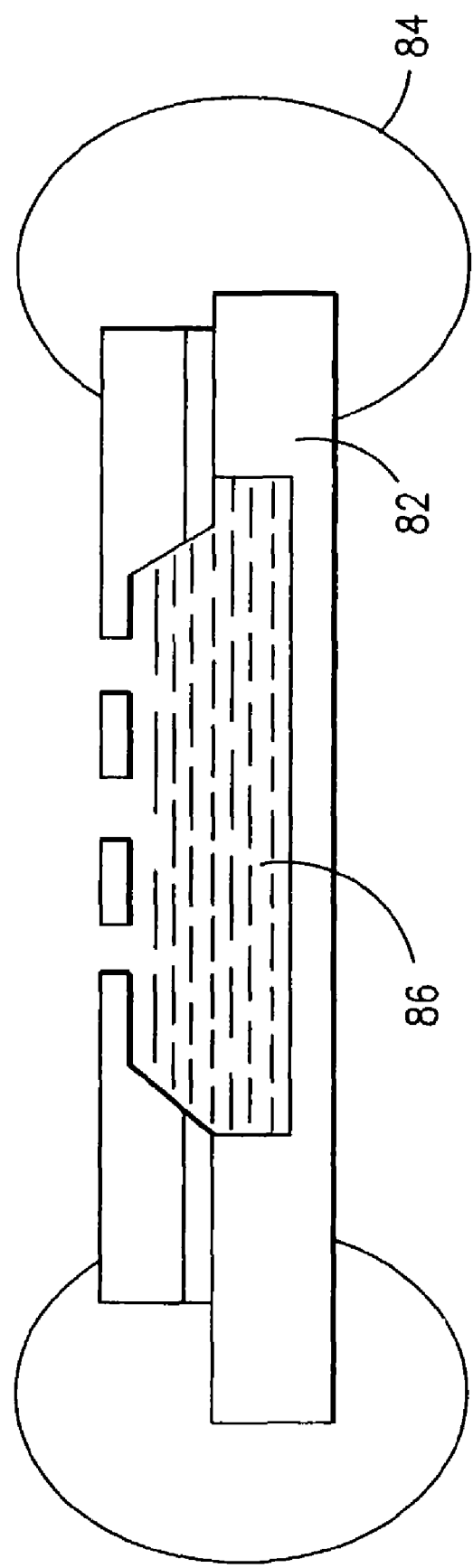
FIG. 6 represents a cross-sectional view of an embodiment of a substrate such as that illustrated in FIG. 4e and an embodiment of a fluid reservoir clamped to the substrate.

FIG. 6 illustrates the substrate shown in FIG. 4e and a fluid reservoir 82 attached to the substrate. The reservoir could be any suitable material. For example, the reservoir could be glass, ceramic, or silicon.

To prevent the substrate and the reservoir from shifting positions relative to each other, the reservoir may be secured to the substrate. Any suitable means may be utilized for securing the reservoir to the substrate. For example, clamps 84 could be utilized to secure the substrate and reservoir to each other. After arranging the substrate and the reservoir adjacent to each other, the denaturing fluid 86 may be supplied to the space defined the reservoir and the substrate.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

I claim:

1. A means for storing information in a double stranded nucleic acid molecule, comprising:
   a substrate having defined therein an array of periodically-spaced regions;
   at least one double stranded nucleic acid molecule disposed on the substrate such that a plurality of periodically-spaced regions from among the array of periodically-spaced regions is in contact with the double stranded nucleic acid molecule;
   a means for denaturing a portion of the double stranded nucleic acid molecule adjacent to one region from among the plurality of periodically-spaced regions by heating; and
   at least one insertion compound attached to the denatured portion of the double stranded nucleic acid molecule,
   wherein information stored in the double stranded nucleic acid molecule is defined by the presence or absence of the insertion compound.

2. A device for storing information in a double stranded nucleic acid molecule comprising:
   a substrate having defined therein an array of periodically spaced regions;
   at least one double stranded nucleic acid molecule disposed on the substrate such that a plurality of periodically regions from among the array of periodically spaced regions is in contact with the double stranded nucleic acid molecule; and
   a reservoir for storing a denaturing solution arranged adjacent to the substrate, the denaturing solution preferentially wetting the periodically spaced regions; and
   the denaturing solution further comprising an insertion compound.

3. The device of claim 2, wherein storing of information is defined by the presence or absence of the insertion compound.

4. The device of claim 2, wherein the insertion compound includes an attachment portion and a detection portion.

5. The device of claim 2, wherein denaturation is accomplished by passing electrical current though a metal element arranged in or on the substrate.

6. The device of claim 3, wherein said denaturation is accomplished by contacting said nucleic acid molecule with a solution capable of denaturing a nucleic acid molecule.

7. The device of claim 6, wherein the solution is aqueous.

8. The device of claim 2, wherein said periodically spaced regions have different wetting properties.

9. The device of claim 8, wherein said periodically spaced regions are organized as a plurality of lines.

10. The device of claim 9, wherein the lines comprise a first type having a first wetting property and a second type having a second wetting property.

11. The device of claim 2, wherein said periodically spaced regions include channels.

12. The device of claim 11, wherein said channels are all of the same depth.

13. The device of claim 12, wherein said depth is about 10 nanometers to about 500 nanometers.

14. The device of claim 11, wherein said channels are all of the same width.

15. The device of claim 9, wherein all lines are parallel.

16. The device of claim 2, wherein the substrate includes at least one semiconductor material.

17. The device of claim 16, wherein the substrate is a silicon wafer.

18. The device of claim 2, wherein said periodically spaced regions comprise at least one metal arranged on the surface of said regions.

19. The device of claim 11, further comprising a portion of a dielectric material overhanging openings to the channels.

20. The device of claim 2, further comprising an optical detector.

* * * * *